US011474050B2

(12) United States Patent
Read et al.

(10) Patent No.: US 11,474,050 B2
(45) Date of Patent: Oct. 18, 2022

(54) RADIATION DETECTOR MODULE WITH INSULATING SHIELD

(71) Applicant: REDLEN TECHNOLOGIES, INC., Saanichton (CA)

(72) Inventors: Christopher Read, Victoria (CA);
Keira Flanagan, North Saanich (CA);
Michael Ayukawa, Victoria (CA);
Jeffrey Allan Walton, Duncan (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 41 days.

(21) Appl. No.: 17/193,219

(22) Filed: Mar. 5, 2021

(65) Prior Publication Data
US 2021/0285897 A1    Sep. 16, 2021

Related U.S. Application Data

(60) Provisional application No. 62/988,111, filed on Mar. 11, 2020.

(51) Int. Cl.
*G01N 23/046*    (2018.01)
*G01N 23/083*    (2018.01)

(52) U.S. Cl.
CPC ......... *G01N 23/046* (2013.01); *G01N 23/083* (2013.01); *G01N 2223/04* (2013.01); *G01N 2223/30* (2013.01); *G01N 2223/419* (2013.01); *G01N 2223/501* (2013.01)

(58) Field of Classification Search
CPC ............... G01N 23/046; G01N 23/083; G01N 2223/04; G01N 2223/30; G01N 2223/419; G01N 2223/501; A61B 6/44; A61B 6/4266; A61B 6/032; A61B 6/4258; A61B 6/4291
See application file for complete search history.

(56) References Cited

U.S. PATENT DOCUMENTS

| | | | |
|---|---|---|---|
| 5,668,851 A * | 9/1997 | Dobbs ................. | A61B 6/4291 378/7 |
| 10,393,891 B2 | 8/2019 | Iniewski et al. | |
| 10,396,109 B2 | 8/2019 | Iniewski et al. | |
| 2004/0136493 A1* | 7/2004 | Konno ................. | A61B 6/032 378/19 |
| 2017/0290555 A1 | 10/2017 | Iniewski et al. | |
| 2017/0322319 A1 | 11/2017 | Iniewski et al. | |
| 2019/0339402 A1 | 11/2019 | Crestani et al. | |

* cited by examiner

*Primary Examiner* — Courtney D Thomas
(74) *Attorney, Agent, or Firm* — The Marbury Law Group PLLC

(57) ABSTRACT

A radiation detector module includes a frame, a module circuit board connected to the frame, detector units that each include radiation sensors disposed above the frame and electrically connected to the module circuit board, and an optically and infrared radiation opaque, X-ray transparent, electrically insulating detector shield covering a top surface and at least one side surface of the radiation sensors.

20 Claims, 10 Drawing Sheets

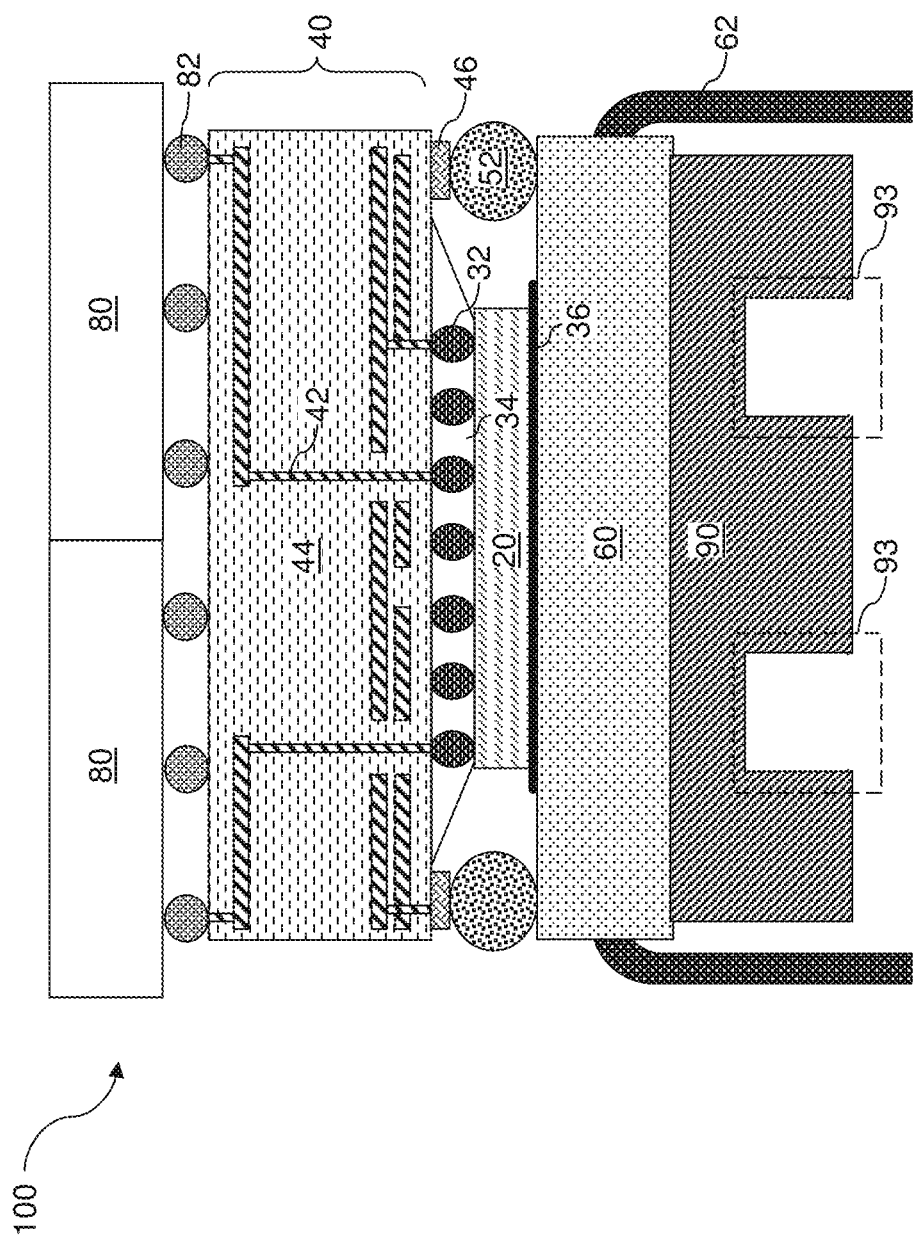

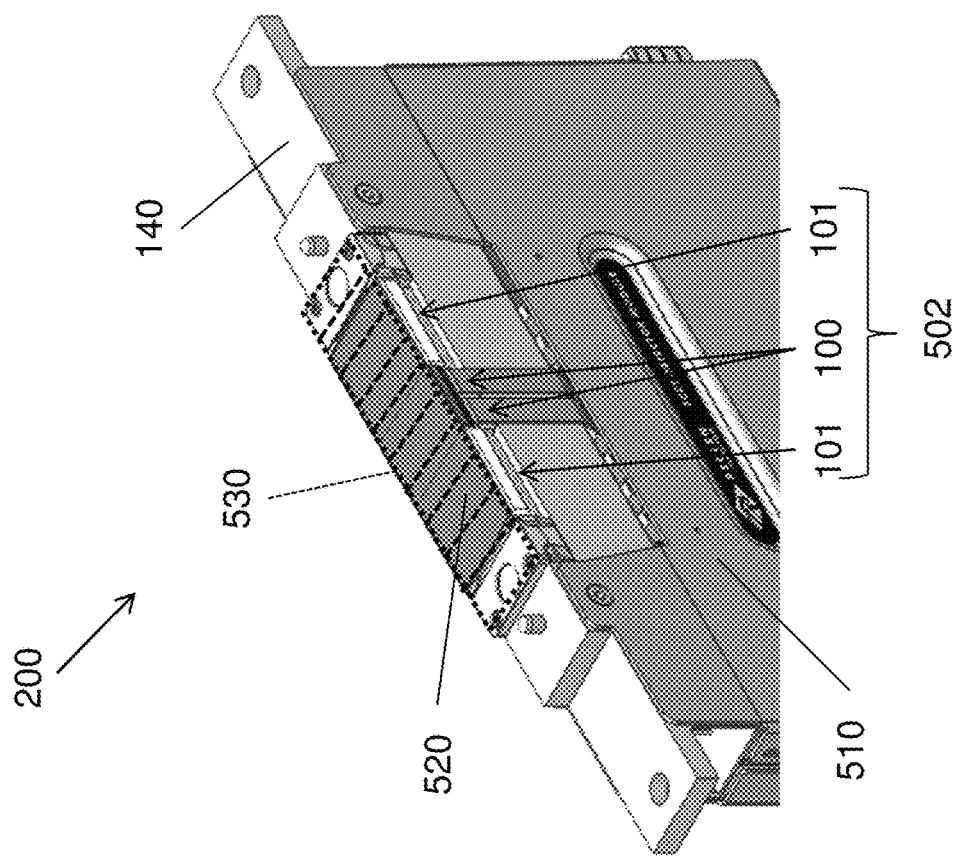
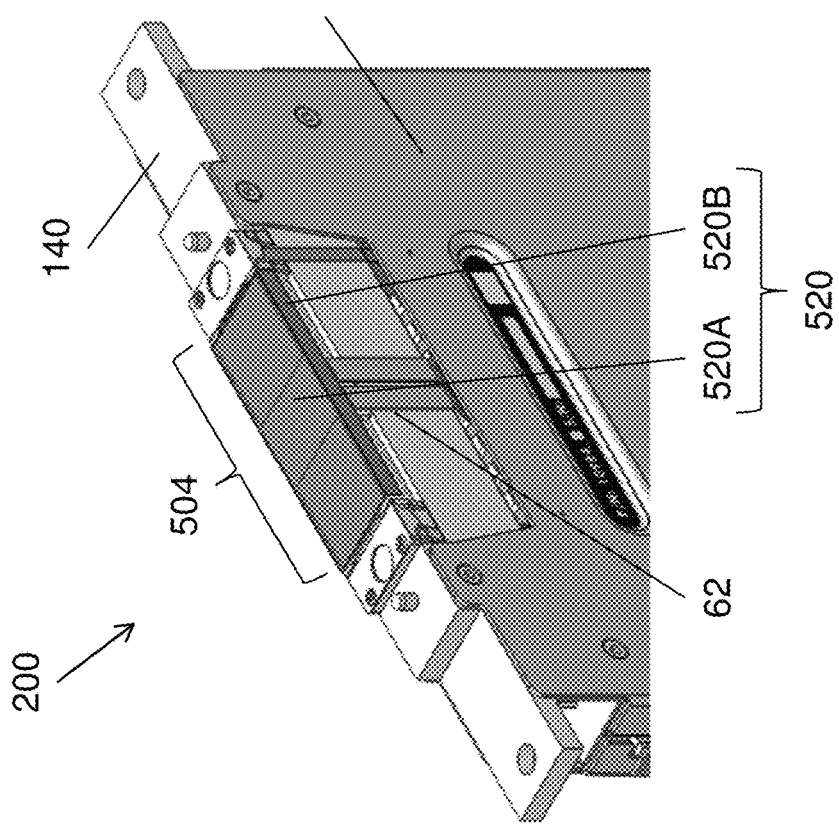
FIG. 5B
FIG. 5A

RADIATION DETECTOR MODULE WITH INSULATING SHIELD

FIELD

The present invention relates generally to gamma-ray and X-ray detectors, and more specifically to an X-ray detector module with an insulating shield.

BACKGROUND

Room temperature pixelated radiation detectors made of semiconductors, such as cadmium zinc telluride ($Cd_{1-x}Zn_xTe$ where $0<x<1$, or "CZT"), are gaining popularity for use in medical and non-medical imaging. These applications use high energy resolution and sensitivity of the radiation detectors.

SUMMARY

According to various embodiments of the present disclosure, provided is a radiation detector module, comprising: a frame; a module circuit board connected to the frame and comprising a row of board-side connectors; units disposed on the frame such that top surfaces of the units form a planar detection surface on top of the frame, the units comprising detector units that each comprise a radiation sensor disposed above the frame, an interposer, an application-specific integrated chip (ASIC), a carrier board, and a flex cable assembly electrically connected to one of the board-side connectors; and an optically opaque, X-ray transparent, dielectric detector shield covering the detection surface.

According to various embodiments of the present disclosure, provided is a detector array comprising: an array frame; and radiation detector modules connected to the array frame, such that the detection surfaces of the detector modules are exposed through the array frame.

According to various embodiments of the present disclosure, a radiation detector module includes a frame, a module circuit board connected to the frame, detector units that each include radiation sensors disposed above the frame and electrically connected to the module circuit board, and an optically and infrared radiation opaque, X-ray transparent, electrically insulating detector shield covering a top surface and at least one side surface of the radiation sensors.

BRIEF DESCRIPTION OF THE DRAWINGS

FIG. 2B is a vertical cross-sectional view of an alternative configuration of the radiation detector unit according to another embodiment of the present disclosure.

FIGS. 5A and 5B are respectively front and back side perspective views of a detector module according to an embodiment of the present disclosure.

DETAILED DESCRIPTION

An embodiment radiation detector includes a radiation detector module containing an insulating, X-ray transparent and optically opaque shield, such as an insulating polymeric cover sheet, to reduce high voltage arcing and background noise counts due to optical and infrared radiation leakage, the various aspects of which are described herein with reference to the drawings.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

In computed tomography (CT) imaging systems, a scanned object is exposed to an X-ray beam. Attenuated photons from the X-ray beam are detected by a detector array. When an object is loaded in a CT imaging system, the X-ray beam may be heavily attenuated, and the number of photons detected by the detector array may be orders of magnitude less than the number of photons emitted from an X-ray source. For image reconstruction purposes, the detector array can be exposed to a direct X-ray beam without an intervening object located inside the CT imaging system. In such cases, the photon count rates in the CT imaging system may reach values of 100 million counts per second per square millimeter ($Mcps/mm^2$) or more. The detector array is capable of detecting such a wide range of photon count rates.

Figure 1:
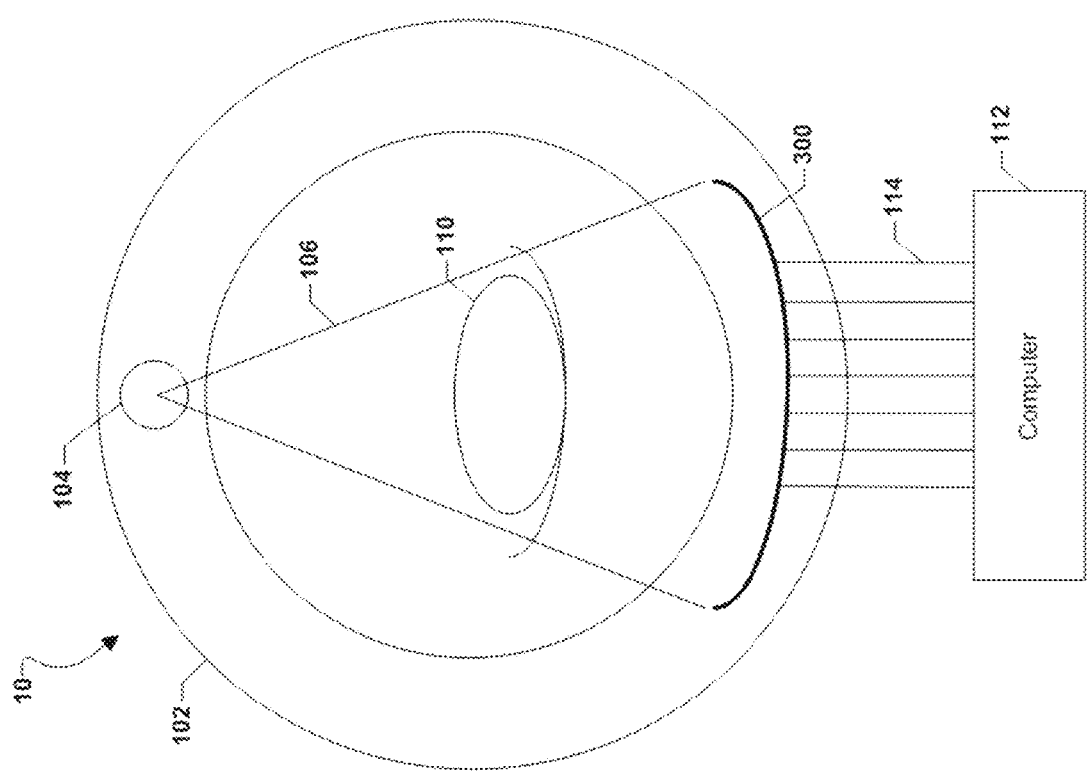
FIG. 1 is a functional block diagram of a computed tomography (CT) imaging system that can be calibrated employing the methods of the present disclosure.

FIG. 1 is a functional block diagram of a CT imaging system 10 according to various embodiments. The CT imaging system 10 may include a gantry 102, which may include a moving part, such as a circular, rotating frame with an X-ray source 104 mounted on one side and a curved detector array 300 mounted on the other side. The gantry 102 may also include a stationary (i.e., non-moving) part, such as a support, legs, mounting frame, etc., which rests on the floor and supports the moving part. The X-ray source 104 may emit a fan-shaped X-ray beam 106 as the gantry 102 and the X-ray source 104 rotates around an object 110 inside the CT imaging system 10. The object 110 may be any biological (e.g., human patient) or non-biological sample to be scanned. After the X-ray beam 106 is attenuated by the object 110, the X-ray beam 106 is received by the detector array 300. The curved shape of the detector array 300 allows the CT imaging system 10 to create a 360° continuous circular ring of the image of the object 110 by rotating the gantry 102 around the object 110.

For each complete rotation of the gantry 102, one cross-sectional slice of the object 110 is acquired. As the gantry 102 continues to rotate, the detector array 300 takes numerous snapshots called "view". Typically, about 1,000 profiles are taken in one rotation of the gantry 102. The object 110 may slowly pass through the rotating gantry 102 so that the detector array 300 captures incremental cross-sectional profiles of the entire object 110. Alternatively, the object 110 may remain stationary and the gantry 102 is moved along the length of the object 110 as the gantry 102 is rotated. The data generated by the detector array 300 is passed to a computer 112 that is located remotely from the gantry 102 via a connection 114. The connection 114 may be any type of wired or wireless connection. If connection 114 is a wired connection, the connection 114 can include a slip ring electrical connection between the rotating part of the gantry 102 supporting the detector 300 and a stationary support part of the gantry 102 which supports the rotating part (e.g., the rotating ring). If the connection 114 comprises a wireless connection, then the detector 300 mounted on the rotating part of the gantry 102 may contain any suitable wireless transceiver to communicate data with another wireless transceiver that is not located on the rotating part of the gantry 102 and which is in communication with the computer 112. The computer 112 may include processing and imaging applications that analyze each profile obtained by the detector array 300, and the full set of profiles from each rotation is compiled to form a two-dimensional image of a cross-sectional slice of the object 110.

Various alternatives to the design of the CT imaging system 10 of FIG. 1 may be employed to practice embodiments of the present disclosure. CT imaging systems may be designed in various architectures and configurations. For example, a CT imaging system may have a helical architecture. In a helical CT imaging scanner, the X-ray source and detector array are attached to a freely rotating gantry. During a scan, a table moves the object smoothly through the scanner creating helical path traced out by the X-ray beam. Slip rings provide the transfer of power and data on and off the rotating gantry. A switched mode power supply may be used to power the X-ray source while at the same time still be small enough to be installed on the gantry.

In other embodiments, the CT imaging system may be a tomosynthesis CT imaging system. In a tomosynthesis CT scanner, the gantry may move in a limited rotation angle (e.g., between 15 degrees and 60 degrees) in order to detect a cross-sectional slice of the object. The tomosynthesis CT scanner may be able to acquire slices at different depths and with different thicknesses that may be constructed via image processing.

The detector array of a CT imaging system may include an array of radiation detector elements, such as pixel sensors. The signals from the pixel sensors may be processed by a pixel detector circuit, which may sort detected photons into energy bins based on the energy of each photon or the voltage generated by the received photon. When a photon is detected, its energy is determined and the photon count for its associated energy bin is incremented. For example, if the detected energy of a photon is 24 kilo-electron-volts (keV), the photon count for the energy bin of 20-40 keV may be incremented. The number of energy bins may range from one to several, such as two to six. In an illustrative example, a photon counting detector may have four energy bins: a first bin for detecting photons having an energy between 20 keV and 40 keV, a second bin for detecting photons having an energy between 40 keV and 60 keV, a third bin for detecting photons having an energy between 60 keV and 80 keV, and a fourth bin for detecting photons having an energy above 80 keV. The greater the total number of energy bins, the better the material discrimination.

The computed tomography (CT) imaging system 10 of the embodiments of present disclosure includes a detector array 300 (which is also known as a detector module system (DMS)). The detector array 300 includes a plurality of detector modules 200 that are arranged in a piecewise curvilinear array such that surfaces of the detector modules conform to the surface of a cylindrical arc. These detector modules are constructed to minimize gaps between adjacent pairs of detector modules. Each detector module is constructed from a set of radiation detector units 100, which are also referred to as "units" or "submodules." The radiation detector units of the present disclosure are designed to minimize gaps between adjacent pairs of radiation detector units. Thus, a two-dimensional array of four side buttable radiation detector units arranged within a curved cylindrical surface can be provided without gaps, or with only minimal gaps, among the radiation detector units.

Figure 2A:
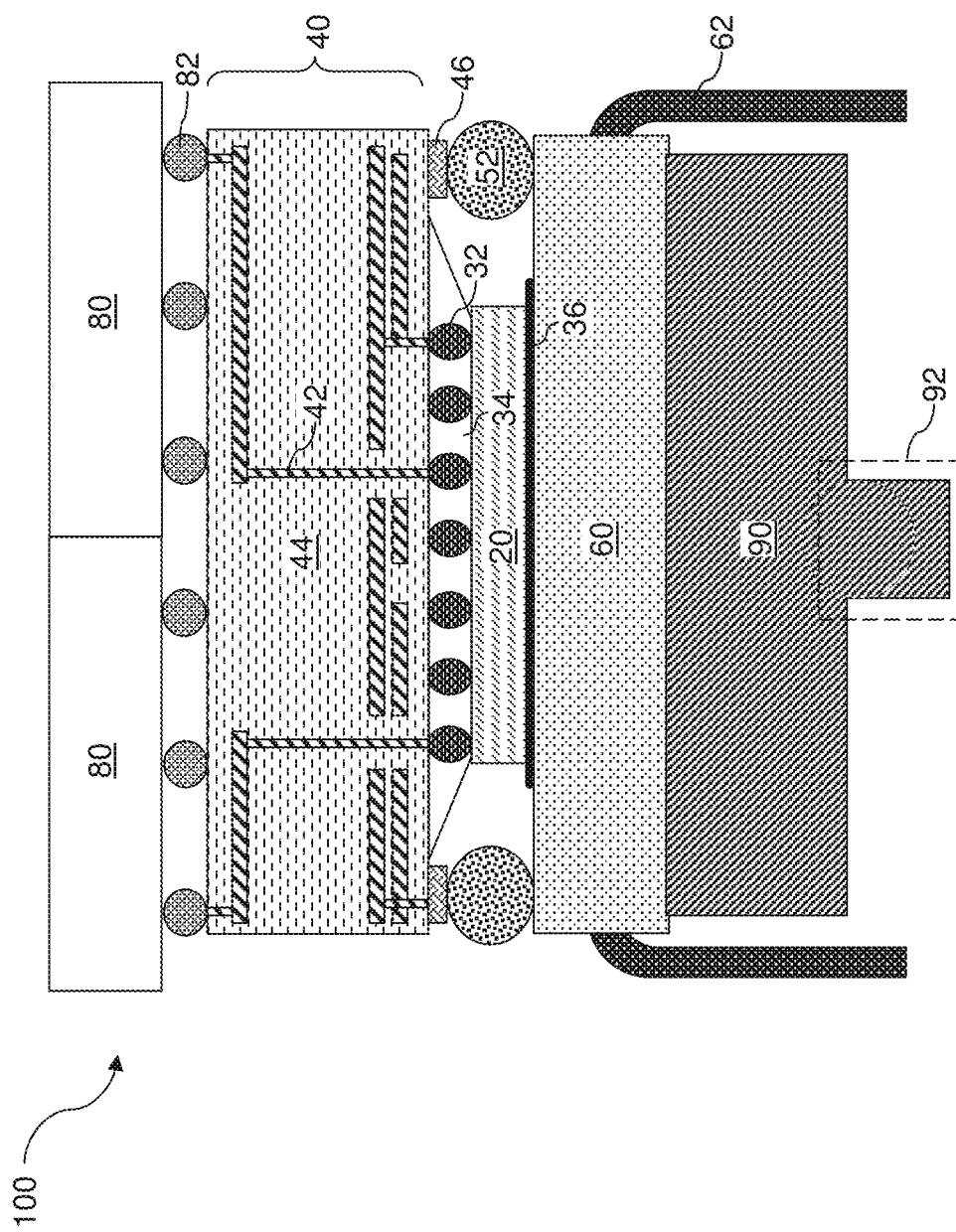
FIG. 2A is a vertical cross-sectional view of a radiation detector unit according to an embodiment of the present disclosure.
Figure 2C:
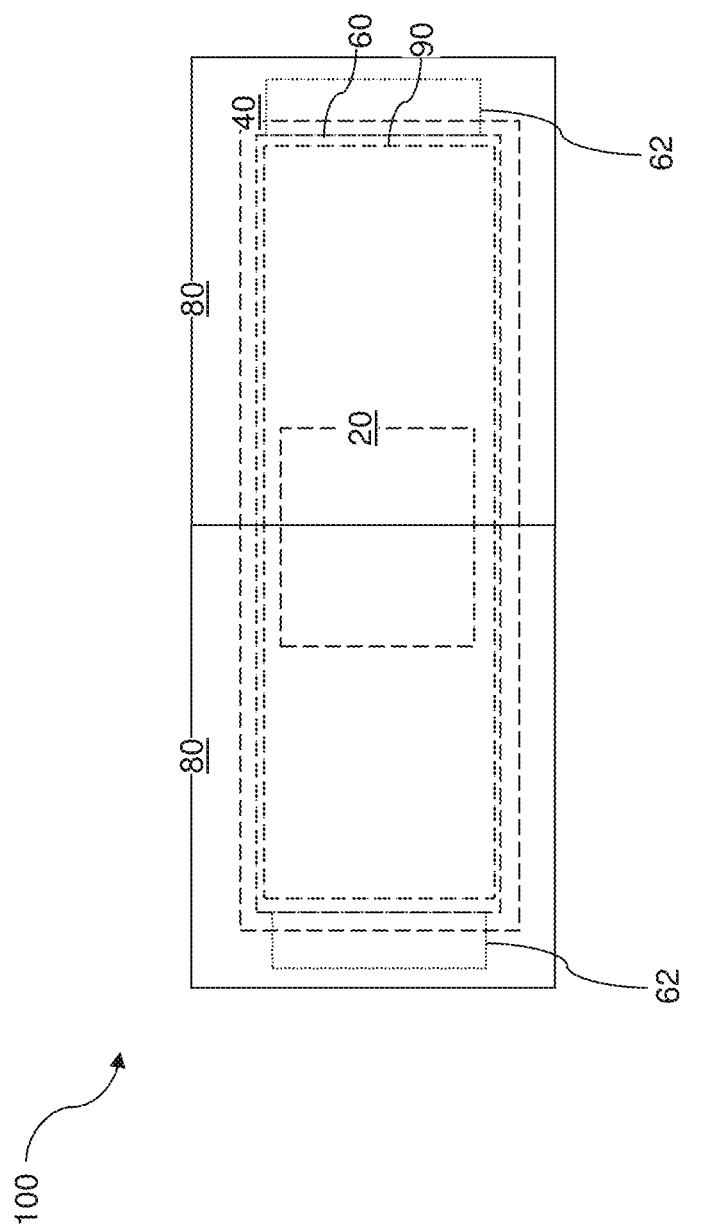
FIG. 2C is a top-down view of the radiation detector units of FIGS. 2A and 2B in which the lateral extents of various underlying components are also illustrated.
Figure 3:
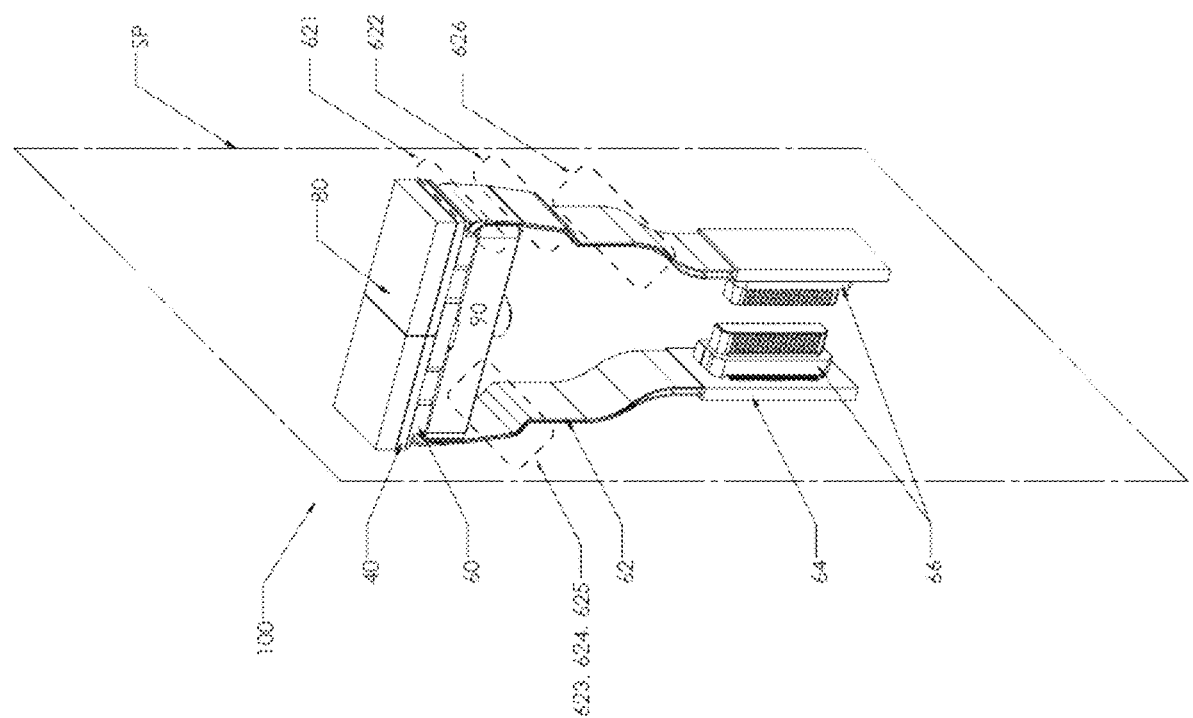
FIG. 3 is a perspective view of the radiation detector unit of FIG. 2A.

Referring to FIGS. 2A, 2C, and 3, various views of a radiation detector unit 100 according to an embodiment of the present disclosure is illustrated. FIG. 2B illustrates an alternative configuration of the radiation detector unit 100 according to another embodiment of the present disclosure. The radiation detector unit 100 of FIG. 2B can be derived from the radiation detector unit of FIGS. 2A, 2C, and 3 by modifying an engagement block 90 to alter the pattern of non-planar features that can be employed to engage a circuit board.

The radiation detector unit 100 of FIGS. 2A-2C and 3 includes a special purpose semiconductor chip configured to receive electrical signals from a set of at least one radiation sensor 80 (such as a pair of radiation sensors 80) as input signals and to generate output signals representing the detection location and the magnitude of the detection current for each detected event. The special purpose semiconductor chip is herein referred to as an application-specific integrated chip 20, or an "ASIC" 20, which is an integrated circuit (IC) chip that is customized for use in the radiation detector unit 100. The ASIC 20 includes an arrangement of electronic signal sensing channels and supporting logic circuitry in at least one monolithic component. The ASIC 20 is configured to identify the pixel at which an event (i.e., impingement of radiation) is detected, to measure the electrical current induced by the event, and to provide digital signals representing the magnitude of the electrical signals (which can be generated by an analog-to-digital conversion (ADC) circuitry). The ASIC 20 interfaces with external components through bonding pads that are located on the front side surface of the ASIC 20. As used herein, the "front side" of elements refers to the side that faces the incoming radiation, and the "backside" of elements refers to the side that is the opposite side of the front side. The bonding pads include input pads, output pads, and power pad. The bonding pad(s) of the ASIC 20 can be arranged as an array, such as a rectangular array.

An interposer 40 is provided. The interposer 40 includes an insulating interposer matrix 44, which includes semiconductor, glass, polymer (e.g., printed circuit board insulating laminate) or ceramic material. The interposer 40 includes inner backside bonding pads (not expressly shown) located at a center region of the backside surface, outer backside bonding pads 46 located at a periphery of the backside surface, and front side bonding pads (not expressly shown) located on the front side surface. The insulating interposer matrix 44 embeds various metal interconnect structures 42 that provide electrical connections among the inner backside bonding pads, the outer backside bonding pads, and front side bonding pads.

The inner backside bonding pads can have the same periodicity as the bonding pads of the ASIC 20. The front side bonding pads can be arranged as an array such as a rectangular array. The front side bonding pads can have the same periodicity as the periodicity of bonding pads provided on the backside of the radiation sensors 80. The outer backside bonding pads 46 can be arranged along the periphery of the backside of the insulating interposer matrix 44. Generally, the periodicity of the front side bonding pads can be different from the periodicity of the inner backside bonding pads. Typically, the pitch of an array of the front side bonding pads can be different than the pitch of an array of the backside bonding pads.

The ASIC 20 is mounted to the backside of the interposer 40 through an array of first bonding structures 32, such as solder balls or copper pillars. Specifically, the array of first bonding structures 32, which are illustrated as solder balls for clarity can be bonded to a respective pair of a bonding pad on the front side of the ASIC 20 and an inner backside bonding pad of the interposer 40 employing a flip-chip bonding process (e.g., a C4 bonding process). If copper pillar bonding structures are used, then they are bonded by a thermo-compression process at an elevated temperature. An insulating matrix 34 can be formed around the array of first bonding structures 32 to structurally reinforce the array of first bonding structures 32. While a configuration in which one ASIC 20 is bonded to the backside of the interposer 40 is illustrated herein, two or more ASIC's 20 may be bonded to the backside of the interposer 40 if necessary. In one embodiment, the ASIC 20 has a smaller cross sectional area in a plane parallel to the major surface of the ASIC than the corresponding cross sectional area of the interposer 40.

The interposer 40 is configured to transmit event detection signals from at least one radiation sensor 80 (which may be a pair of radiation sensors 80) to the ASIC 20, and the ASIC 20 is configured to convert event detection signals from the at least one radiation sensor 80 to digital detection signals, which can include the pixel location and the energy range of the detected radiation. The interposer 40 is configured to transmit power from a carrier board 60 to each of the at least one radiation sensor 80 and to the ASIC 20. The interposer 40 routes event detection signals from the radiation sensors 80, as received through the front side bonding pads, to ASIC pixel input channels as input signals to the ASIC 20 through a respective one of the inner backside bonding pads. The interposer 40 routes control signals and electrical power supply (that are provided through a carrier board 60 and received through the outer backside bonding pads 46) to the ASIC 20 through the inner backside bonding pads. Further, the interposer 40 receives output data generated by the ASIC from the data channels of the ASIC through the inner backside bonding pads, and routes the output data to the carrier board 60 and at least one flex cable assembly 62 through outer backside bonding pads 46.

A carrier board 60 and at least one flex cable assembly 62 are provided, which are configured to route power supply to the ASIC 20 and to the at least one radiation sensor 80, control signals to the ASIC 20, and data signals generated by the ASIC 20 and transmitted through the interposer 40. One end of each flex cable assembly 62 can be attached to a respective side of the carrier board 60, and another end of each flex cable assembly can be connected to an assembly connector of a signal processing board, which is herein referred to as a module circuit board 120 (shown in FIG. 4), which can include a dual minimodule (DMM) board and an optional buffer board. The carrier board 60 can be a printed circuit board including an insulating substrate and printed interconnection circuits. Each flex cable assembly 62 includes signal wires and power wires. The signal wires are configured to transmit the electronic detection signals and control signals, and the power wires are configured to provide electrical power to the interposer 40, which distributes the electrical power to the ASIC 20 and the radiation sensor(s) 80. The flex cable assembly 62 can be more flexible (i.e., can bend with a lower application of force) than the carrier board 60.

Carrier board bonding pads (not expressly shown) can be provided at a periphery of the front side of the carrier board 60. The pattern of the circuit board bonding pads matches the pattern of the outer backside bonding pads 46 of the interposer 40. Each flex cable assembly 62 may be attached to a side of the carrier board permanently or through connectors. If two flex cable assemblies 62 are employed as a pair, the flex cable assemblies 62 can be attached to opposing sides of the carrier board 60.

The assembly including the ASIC 20 and the interposer 40 is attached to the assembly including the carrier board 60 and the at least one flex cable assembly 62. For example, the carrier board 60 can be bonded to the backside of the interposer 40 employing an array of second solder balls 52. Each second solder ball 52 can be bonded to a respective pair of an outer backside bonding pad 46 located on the backside of the interposer 40 and a bonding pad located in a peripheral region of the front surface of the carrier board 60. To avoid damaging the first bonding structures 32 (e.g., to avoid reflowing the first solder balls or damaging the copper pillars), the second solder balls 52 can include a solder material having a lower reflow temperature than the temperature used to bond the first bonding structures 32. For example, the second solder balls 52 can include a solder material having a lower reflow temperature than that solder ball first bonding structures 32 or a lower reflow temperature than a temperature used for the thermo-compression bonding process of the copper pillar first bonding structures 32. In one embodiment, a ball grid array (BGA) solder process can be employed to bond the array of second solder balls 52. A thermally conductive paste 36, such as a silver paste layer, can be formed between the backside of the ASIC 20 and the center portion of the front surface of the carrier board 60 to effectively dissipate heat generated from the ASIC 20. The carrier board 60 can include an electrically insulating matrix providing high thermal conductivity to function as an effective conduit for heat generated from the ASIC 20.

A heat sink comprising an engagement block 90 can be attached to the backside surface of the carrier board 60. The engagement block 90 includes a high thermal conductivity material such as a metal, and includes at least one non-planar feature (92, 93) on the backside to facilitate subsequent mounting the radiation detector unit 100 to a module circuit board 120. For example, the engagement block 90 can be an aluminum block or a copper block including at least one protrusion 92 or at least one recess cavity 93 on the backside. In this case, the module circuit board 120 can be provided with at least one matching non-planar feature to lock in the at least one non-planar feature (92, 93) of the engagement block 90. The engagement block 90 functions as a substrate for structurally holding the carrier board 60 and additional components attached thereto. The engagement block 90 can be attached to the carrier board 60 employing a thermally conductive adhesive such as a thermally conductive paste, and/or by mechanical connection structures (such as snap-in connectors, screws, and/or bolts and nuts). A flat front side surface of the engagement block 90 can be attached to the backside surface of the carrier board 60. In an alternative embodiment, instead of utilizing an engagement block 90 in a shape of thermal heat slug heat sink, the carrier board 60 may include a hole which allows a heat sink post to pass through the hole.

At least one radiation sensor 80 can be bonded to the front side of the interposer 40 employing at least one array of bonding material portions 82. The at least one radiation sensor 80 is bonded to the interposer 40 after bonding the ASIC 20 and the carrier board 60 to the interposer 40. To avoid damage to the first bonding structures 32 (e.g., reflow of the first solder balls or damage to the copper pillars) and the second solder balls 52 during bonding of the radiation sensor(s) 80 to the interposer 40, each radiation sensor 80 can be attached to the top surface (which is also referred to as a "pixel connection surface") of the interposer 40 employing a low temperature bonding material for the bonding material portions 82. The bonding material portions 82 can include a low temperature solder material having a lower reflow or setting temperature than the array of second solder balls 52. In one embodiment, the bonding material portions 82 can include a low temperature solder material or conductive epoxy. For example, the conductive epoxy may be a radiation setting conductive epoxy which is set at a temperature below 60° C., such as at 25 to 55° C., including 45 to 50° C., using radiation to cure the epoxy.

Employing a low temperature solder or epoxy material for the bonding material portions 82 has the advantage of minimizing adverse thermal cycling of the radiation detector (s) 80, which typically includes temperature-sensitive semiconductor materials which can suffer from performance degradation upon exposure to high temperature cycling. Even short exposures to such a high temperature can damage the radiation sensors (such as CZT sensors). Typically, thermal cycling above 200 degrees Celsius should be avoided for the radiation sensor(s) 80. Even use of low temperature solder materials, such as BiSn, entails heating to a temperature above 170 degrees Celsius, and can degrade many types of radiation sensors 80 by impacting contact properties or bulk properties of semiconductor materials. In one embodiment, conductive epoxy which is set below 170° C., such as below 60° C., can be employed for the bonding material portions 82.

In one embodiment, the at least one radiation sensor 80 comprises a pair of radiation sensors 80 having a respective rectangular shape and adjoined to each other with no gap or with a gap less than 3 mm, and/or less than 2 mm, and/or less than 1 mm. The at least one radiation sensor 80 can comprise a radiation-sensitive material selected from cadmium zinc telluride, cadmium telluride, gallium arsenide, silicon, and a scintillator material. Each radiation sensory 80 includes an array of sensing pixels, which may be provided as a prefabricated multi-pixel monolithic component, or an assembly of multiple monolithic components.

Upon mounting of the at least one radiation sensor 80, assembly of the radiation detector unit 100 is complete, and dimensional compliance and functionality of the radiation detector unit 100 can be tested. In order to form a two-dimensional array of multiple the radiation detector units 100, dimensional parameters of each radiation detector unit 100 needs to be in compliance with specification. Defective radiation detector units 100 that do not comply with the dimensional specification or functionality specification can be screened and discarded at this processing step. The screening procedure can be employed to enhance manufacturing yield of detector modules and detector arrays.

The interposer 40 can accommodate variations in pixel patterns in the radiation sensors 80. Without the interposer 40, a change in the pixel pattern of the radiation sensors 80 would require a change in the ASIC footprint and the bonding connection pattern. According to as aspect of the present disclosure, the same ASIC 20 can be employed in combination with many different radiation sensors having different pixel patterns by merely changing the interposer 40 to accommodate such changes. In other words, the interposer 40 permits the use of an ASIC 20 having a different bonding pad arrangement than the bonding pad arrangement on the backside of the radiation sensors 80. Thus, an ASIC 20 of a same design can be employed in combination with many different types of radiation sensors 80 by changing the design of the interposer 40.

Further, the interposer provides outer backside bonding pads 46 for providing electrical connection with the carrier board 60, and therefore, there is no need to provide bonding pads on both sides of an ASIC in the configuration of the embodiments of the present disclosure. A thermally conductive paste 36 can be used to bond the backside of the ASIC 20 to the carrier board 60, to provide additional thermal management. The interposer 40 routes input signals for the ASIC pixel input channels from the front side to the backside, and data from the data channels of the ASIC 20 from a center region of the backside surface to a peripheral region of the backside surface. Thus, the interposer 40 adapts, redistributes, and physically separates the ASIC input channel connections from the ASIC power connections and from data and control signals.

In one embodiment shown in FIG. 3, the radiation detector unit 100 can have a mirror symmetry about a symmetry plane SP that includes the interface between a pair of radiation sensors 80. The total area of the at least one radiation sensor 80 (e.g., two sensors 80 shown in FIG. 3) can be greater than the horizontal cross-sectional areas of underlying components of the radiation detector unit 100. Thus, the outer peripheries of the interposer 40, the ASIC 20, the carrier board 60, and the engagement block 90 are located entirety within the outer periphery of the at least one radiation sensor 80 in a top-down view (such as the view of FIG. 2C). Further, the at least one flex cable assembly 62 generally stretches backward upon application of a suitable force along a backside direction, i.e., away from the at least one radiation sensor 80. By limiting the lateral extent of all components along a direction perpendicular to the front side surface(s) of the at least one radiation sensor 80, the radiation detector unit 100 can be in a compact shape that allows stacking in two orthogonal directions, which can be the directions perpendicular to the lengthwise edges and the widthwise edges of the at least one radiation sensor 80.

According to an aspect of the present disclosure, a radiation detector unit 100 is provided, which comprises: at least one radiation sensor 80 bonded to a front side of an interposer 40; an application-specific integrated chip (ASIC) 20 bonded to a backside of the interposer 40; a carrier board 60 bonded to the backside of the interposer 40 and located on a backside of the ASIC 20; at least one flex cable assembly 62 attached a respective side of the carrier board 50 and including signal wires and power wires; and an engagement block 90 including a flat front side surface contacting a backside surface of the carrier board 60 and a non-planar backside surface including at least one engaging surface feature (92, 93). In one embodiment, each of the interposer 40, the ASIC 20, the carrier board 60, and the engagement block 90 has a respective cross-sectional area within two-dimensional planes that are parallel to a front side surface of the interposer 40 such that lateral extents of the interposer 40, the ASIC 20, the carrier board 60, and the engagement block 90 are entirely within an area defined by a cross-sectional area of the at least one radiation sensor 80 within a two-dimensional plane that is parallel to the front side surface of the interposer 40.

In one embodiment, the interposer 40 can be configured to transmit event detection signals from the at least one radiation sensor 80 to the ASIC 20, and the ASIC 20 can be configured to convert event detection signals from the at least one radiation sensor 80 to digital detection signals. The interposer 40 can be configured to transmit power from the carrier board 60 to each of the at least one radiation sensor 80 and to the ASIC 20. The signal wires are configured to transmit the electronic detection signals and the power wires configured to provide electrical power to the interposer.

In one embodiment shown in FIG. 3, the at least one flex cable assembly 62 comprises a pair of flex cable assemblies 62 attached to two opposing sides of the carrier board 60. The pair of flex cable assemblies 62 provide a lateral extent within horizontal planes that are parallel to the front side surface of the interposer 40 that is located entirely within the area defined by the cross-sectional area of the at least one radiation sensor 80 within the two-dimensional plane upon extension away from the at least one radiation sensor 80, for example, by pulling or by gravity when held up so that the top surface(s) of the at least one radiation sensor 80 face(s) upward. In one embodiment, each of the pair of flex cable assemblies 62 includes a respective snap-in connector 66 at a distal end that is distal from the carrier board 60. Each snap-in connector 66 can be attached to an insulating cover of a respective flex cable assembly 62 by a respective reinforcement mold 64, which provides structural durability to the snap-in connector 66.

In one embodiment, each of the pair of flex cable assemblies 62 can include a first bend region 621 connected directly to a respective side of the carrier board 60 and bending away from the interposer 40; a first straight region 622 connected to the first bend region 621 extending away from the at least one radiation sensor 80 along a normal direction that is perpendicular to the front side surface of the interposer 40; a second bend region 623 connected to the first straight region 622 and bending toward opposite flex cable of the pair of flex cable assemblies 62 (i.e., toward the symmetry plane SP); a second straight region 624 connected to the second bend region 623 and positioned non-perpendicularly (e.g., diagonal or substantially parallel) to a backside of the engagement block 90; a third bend region 625 connected to the second straight region 624 and bending away from the engagement block 90; and a third substantially straight region 626 connected to the third bend region 625 and extending away from the backside of the engagement block 90. The third substantially straight region 626 can be indirectly connected to the snap-in connector 66 via one or more additional bend and/or straight regions. Alternatively, the third substantially straight region 626 can be connected directly to the to the snap-in connector 66. The combination of the bends in the pair of flex cable assemblies 62 causes the volume occupied by the pair of flex cable assemblies 62 to be entirely within a volume generated by extending the outer periphery of the at least one radiation sensor 80 along a direction perpendicular to the front surface of the at least one radiation sensor 80. Assembly of multiple the radiation detector units 100 in a two-dimensional array can be subsequently performed by limiting the lateral extent of each radiation detector unit 100 within a respective volume generated by extending the outer periphery of the at least one radiation sensor 80 of each radiation detector unit 100 along a direction perpendicular to the front surface of the at least one radiation sensor 80.

In one embodiment, the snap-in connectors 66 of the pair of flex cable assemblies 62 include two sets of connection pins that face each other about a two-dimensional plane (i.e., the symmetry plane SP) that is parallel to the two opposing sides of the carrier board 60 and bisects the carrier board 60. In one embodiment, the ASIC 20 is bonded to the to the backside of the interposer 40 by an array of first bonding structures 32, such as solder balls or copper pillars embedded within an insulating matrix 34, and the backside of the ASIC 20 is thermally connected to a front side of the carrier board 60 by a thermally conductive paste 36.

In one embodiment, the carrier board 60 is bonded to the backside of the interposer 40 through an array of second solder balls 52 having a reflow temperature that is lower than a reflow temperature of the array of first solder ball bonding structures 32. The array of second solder balls 52 laterally surrounds the ASIC 20. Each of the at least one radiation sensor 80 is bonded to the front side of the interposer 40 by a respective array of bonding material portions 82 having a reflow or setting temperature than is lower than the reflow temperature of the second solder balls 52.

The interposer 40 may be configured to bond a single radiation sensor 80, a pair of radiation sensors 80, or a K×L matrix of radiation sensors 80 in which K is an integer greater than 1 and L is an integer greater than 1. Each of the radiation sensors 80 can have a rectangular periphery. In case multiple radiation sensors 80 are mounted to the interposer 40, the interposer 40 can be arranged to provide a rectangular outer periphery to provide an abutting configuration upon assembly of multiple radiation detector units 100 in a two-dimensional array.

In one embodiment, the interposer routing structure may employ a core layer that separates pixel connections (low noise) from logic and power supply connections. This is advantageous because noise separation can be maintained between logic signals and noisy power supplies.

The shape and functionality of the radiation detector unit 100 may be optimized to enhance the manufacturability and yield of conversion materials and electronic components within the radiation detector unit 100, and to provide more sensitive and reliable X-ray detection. Further, the radiation detector unit 100 may be optimized to enhance the ability to position the array of radiation sensor pixels in a predefined position, to match other imaging elements in a detector array. Further, the radiation detector unit 100 may be optimized to enhance the ability to connect the array of detector sensing pixels to the electronic sense circuitry in the ASIC 20. In addition, the radiation detector unit 100 may be optimized to enhance the ability to provide the power supply and control signals, and to deliver the data transmission needs to the module circuit board 120, as shown in FIG. 4.

Generally, a radiation detector unit 100 may contain one or more radiation sensor 80, an interposer 40, and at least one ASIC 20. The flex cable assemblies 62 are configured to be able to support all transmission requirements for power supply, control signals, and data signals for the various components within the radiation detector unit 100.

Figure 4:
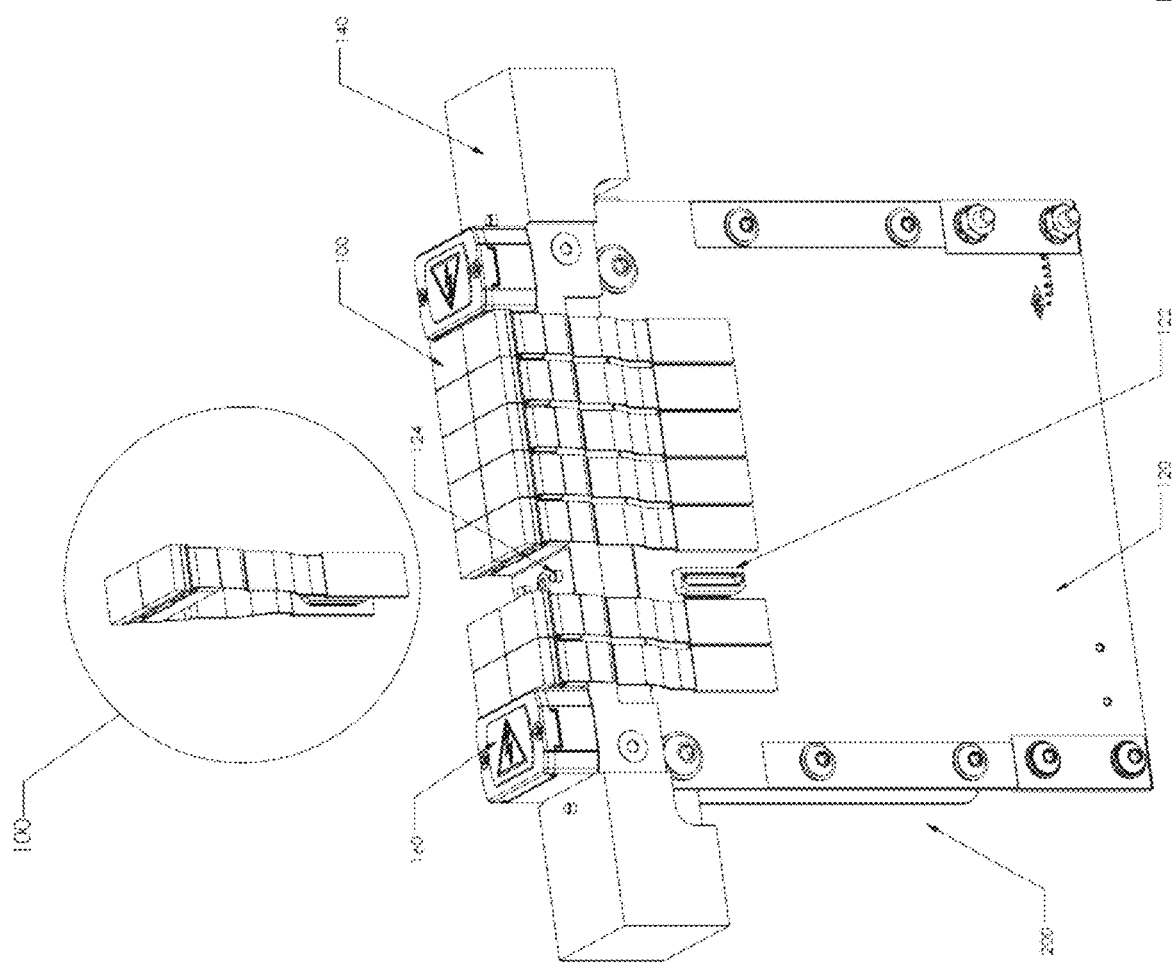
FIG. 4 is a perspective view of a detector module during assembly according to an embodiment of the present disclosure.

Referring to FIG. 4, a detector module 200 can be assembled by providing a module circuit board 120 and a plurality of the radiation detector units 100 described above. The module circuit board 120 can include a pair of major surfaces, which can be planar surfaces on which circuit elements and interconnection traces are printed. As used herein, a major surface of a structure refers to a surface having a surface area of at least 50% of the surface area of the largest surface of the structure. The module circuit board 120 includes at least one row of board-side connectors 122 on at least one major surface. Each board-side connector 122 can have a matching configuration to connect with a snap-in connector 66 of a flex cable assembly 62. In one embodiment, a first row of board-side connectors 122 can be provided on a first major surface of the module circuit board 120, and a second row of board-side connectors 122 can be provided on a second major surface of the module circuit board 120, which is the opposite side of the first major surface. Each board-side connector 122 can be connected to a respective snap-in connector 66. If the snap-in connector 66 contains pins, then the board-side connector 122 can contain recesses, and vice-versa.

The plurality of the radiation detector units 100 can be arranged in a row along an edge of the module circuit board 120. The edge of the module circuit board 120 can include a sidewall that is perpendicular to the at least one major surface of the module circuit board 120. Each of the at least one flex cable assembly 62 can be connected to a respective board-side connector through a respective snap-in connector 66. In one embodiment, the edge of the circuit board includes a row of matching engaging surface features 124, i.e., a surface feature that is the complement of the non-planar feature (92, 93) on the backside of the engagement block 90. For example, an interlocking pair of a protrusion 92 and a cavity 124 (or cavity 93 and protrusion 124) may be employed to secure each attached radiation detector unit 100 to the edge of the module circuit board 120. In one embodiment, each of the matching engaging features 124 locks in a respective one of the at least one engaging surface feature (92, 93) of the plurality of the radiation detector units 100 of the present disclosure, and structurally securing the plurality of the radiation detector units 100.

The module circuit board 120 may be fitted onto a mounting frame 140, such as a metal frame, to facilitate assembly of multiple detector modules into a detector array. Optionally, end holders 160 may be employed at either end, or both ends, of a row of radiation detector units 100 to structurally secure the radiation detector units 100 in the row.

In one embodiment, the at least one flex cable assembly 62 can comprise a pair of flex cable assemblies 62 attached to two opposing sides of the carrier board 60. The pair of flex cable assemblies 62 provide a lateral extent within horizontal planes that are parallel to the front side surface of the interposer 40 such that the lateral extent of flex cable assemblies 62 is located entirely within the area defined by the cross-sectional area of the at least one radiation sensor 80 within the two-dimensional plane upon extension away (for example, by being snapped into a matching board-side connector) from the at least one radiation sensor 80 for each radiation detector unit 100. The snap-in connectors 66 of each pair of flex cable assemblies 62 of the plurality of the radiation detector units 100 can be snapped into a respective board-side connector located on the module circuit board 120.

The plurality of the radiation detector units 100 can be attached to the edge of the module circuit board 120 by engaging each of the at least one engaging surface feature (92, 93) with a row of matching engaging surface features 124 provided at the edge of the module circuit board 120, and by connecting each of the at least one flex cable assembly 62 to the respective board-side connector 122 through a respective snap-in connector 66. In one embodiment, the at least one flex cable assembly 62 of each radiation detector unit 100 comprises a pair of flex cable assemblies 62 attached to two opposing sides of the carrier board 120 via a first row of board-side connectors 122 is located on a first major surface of the module circuit board 120, and a second row of board-side connectors 122 is located on a second major surface of the module circuit board 120 that is located on an opposite side of the module circuit board 120. A first flex cable assembly 62 of each pair of flex cable assemblies 62 of the plurality of the radiation detector units 100 can be connected to a respective one of the board-side connectors 122 within the first row of board-side connectors 122, and a second flex cable assembly 62 of each pair of flex cable assemblies 62 of the plurality of the radiation detector units 100 can be connected to a respective one of the board-side connectors 122 within the second row of board-side connectors 122.

In one embodiment, each radiation sensor 80 within the plurality of the radiation detector units 100 can have a front side surface that is substantially perpendicular to the major surface of the module circuit board 120. In one embodiment, a front side surface of the at least one radiation sensor 80 within each radiation detector unit 100 can have a rectangular shape having a pair of lengthwise edges along a lengthwise direction and a pair of widthwise edges that are shorter than the lengthwise edges along a widthwise direction. The plurality of the radiation detector units 100 can be assembled such that lengthwise edges of each pair of neighboring the radiation detector units abut, i.e., are in direct physical contact with each other.

The radiation detector unit 100 provides mechanical stability and planarity attributes for precision assembly of a detector module and a detector array. The radiation detector unit 100 provides sufficient thermal conduction through the engagement block 90 which acts as a heat sink to remove the heat generated by the ASIC 20 during operation. The heat can be transferred to a detector module thermal management frame assembly.

As discussed above, each radiation detector unit 100 can be tested for functionality and dimensional compliance before assembly into a one-dimensional array of radiation detector units 100 within a detector module 200. A completed detector module 200 can be tested for dimensional compliance and functionality. Should any defect be found among any of the radiation detector units 100, any defective radiation detector unit 100 can be replaced with a functional one to provide a functionally and dimensionally compliant detector module 200. Thus, yield of the detector modules 200 can be managed with a high likelihood of reparability for defective modules. During repair of the detector module 200, the defective radiation detector unit 100 can be removed and replaced without removing the remaining functional detector units 100 from the detector module 200.

FIGS. 5A and 5B are perspective views respectively showing first and second sides of detector module 200 with one or more shields, according to various embodiments of the present disclosure. The detector module 200 is similar to the detector module 200 of FIG. 4, so only the differences therebetween will be discussed in detail.

Referring to FIGS. 5A, and 5B, the detector module 200 includes units 502 disposed on the mounting frame 140. The units 502 include one or more detector units 100 and optionally one or more dummy units 101. In particular, the detector module 200 is shown to include two detector units 100 and two dummy units 101, rather than 8 detector units 100 as shown in FIG. 4. However, the detector module 200 is not limited to any particular number of detector units 100 and dummy units 101. For example, the detector module 200 may include 8 detector units 100 and no dummy units 101.

The detector units 100 may be attached to the module circuit board 120 of the detector module 200 by respective flex cable assemblies 62, as discussed above. The dummy units 101 may be disposed on the mounting frame 140, so as to cover and/or protect the engagement features 124 of the mounting frame 140. The dummy units 101 may be box-shaped components that have a height that is approximately equal to the combined thicknesses of the engagement block 90, carrier board 60, interposer 40, and radiation sensors 80 of the detector units 100. The dummy units 101 are not electrically connected to the module circuit board 120, and are electrically inactive. The tops of the dummy units 101 have the about the same length and width as the tops detector units 100. The dummy units 101 are provided to fill the empty space between the active detector units 100 and the mounting frame 140, in case the mounting frame 140 is designed to hold more detector units 100 than the number of detector units provided for a particular module. Since the dummy units 101 do not function as X-ray detectors, the dummy units 101 may be formed of an electrically insulating material, and may exclude the flex cable assemblies 62 or other functional components of the detector units 100. The dummy units 101 may include features that mate with the engagement features 124, to secure the dummy units 101 to the frame 140.

Accordingly, the units 502 may collectively form a substantially planar detection surface 504 on top of the frame 140. The detection surface 504 may be formed by top surfaces of the dummy units 101 and top surfaces of the radiation sensors 80 of the detector units 100.

In various embodiments, the detector module 200 may also include side shields 510 disposed on each side thereof over the module circuit board 120. The side shields 510 may be attached to the frame 140, using any suitable method, such as by using screws, rivets, clamps, or the like. The side shields 510 may operate to protect the module circuit board 120. The side shields 510 may be formed of an electrically insulating material, such as a polymer material, or the like.

The detector module 200 may also include a detector shield 520 disposed on the units 502. In particular, the detector shield 520 may include a first portion 520A that covers the front surfaces of the unit 502, (e.g. the top surface of each detector unit 100 and optionally the dummy unit 101, as shown in FIGS. 5A and 5B). In other words, the first portion 520A may cover the detection surface 504 of the detector module 200.

Figure 6:
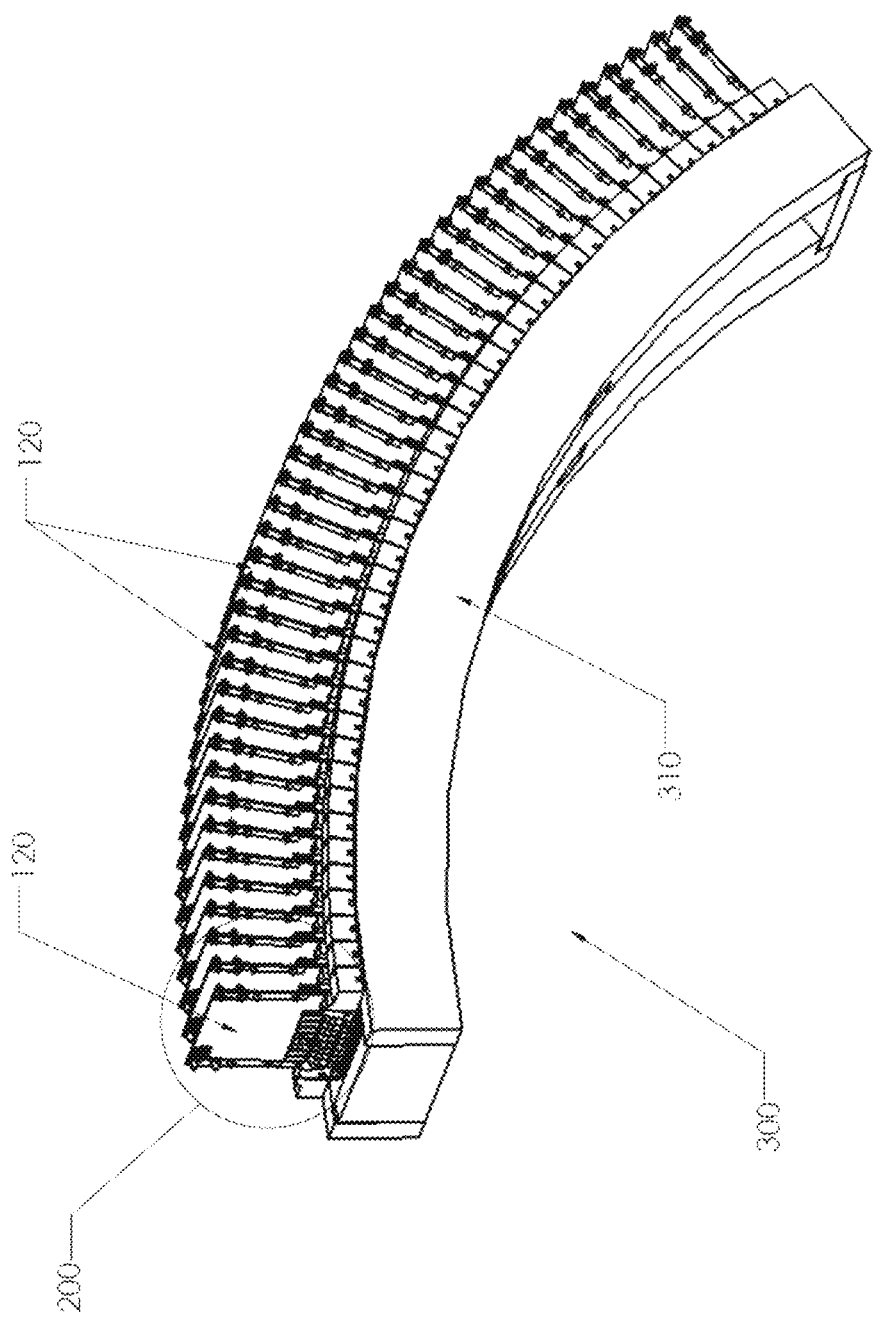
FIG. 6 is a perspective view of a detector array according to an embodiment of the present disclosure.

The detector shield 520 may also include a second portion 520B that extends at an angle form the first portion 520A and covers one or both side surfaces of the units 502 (e.g., covers a first side of the detector units 100 and optionally the first side of the dummy units 101). For example, the second portion 520B may cover at least the side surface of each radiation sensor 80 and optionally corresponding side surfaces of the dummy units 101, on one side of the detection surface 504. The opposite second side of the units 502 (i.e., the detector units 100 and optionally the dummy units 101) may remain uncovered, since the second side of the units 502 may contact the second portion of the detector shield of an adjacent detector module 200 mounted in the same array 300, as shown in FIG. 6.

The detector shield 520 may be optically and infrared opaque, X-ray and optionally gamma ray transparent, and may have a high dielectric strength. For example, the detector shield 520 may block at least 95%, such as at least 99%, or at least 99.9% of incident visible and infrared light, and may transmit least 95%, such as at least 99%, or at least 99.9% of incident X-rays (e.g., X-rays having an energy ranging from about 20 KeV to about 160 KeV). The detector shield 520 may be electrically insulating at voltages of −1000V or more. For example, the detector shield 520 may have a dielectric strength of at least 2000 V/mil, such as 2000 to 2800 V/mil, or higher at voltages of −1000V to −1500V.

In some embodiments, the detector shield 520 may be formed of any suitable polymer material, such as a polyethylene terephthalate (PET) material, a polyimide material, or the like. For example, the detector shield 520 may be formed a Kapton™ 100B polyimide film manufactured by the DuPont Company.

The detector shield 520 may be in the form of a film or tape have a thickness ranging from about 15 to about 50 μm, such as a thickness ranging from about 25 to about 40 μm. Accordingly, the detector shield 520 may be attached to the detector module 200 by an adhesive material or layer. However, in other embodiments, the detector shield 520 may be attached to the detector module 200 by any other suitable method, such as by friction fit, clamping, etc.

Accordingly, the detector shield 520 may operate to prevent the generation of background noise due to visible light and/or infrared radiation striking the radiation sensors 80 during use. In addition, the detector shield 520 may prevent human exposure to high voltage during use, servicing, and/or installation.

The detector shield 520 may also operate to protect the detector module 200 from physical damage during installation. Further, the detector shield 520 may prevent arcing and or electrical contact between adjacent detector modules 200 when the detector modules 200 are installed in the detector array 300, as discussed below with regard to FIG. 6. For example, the second portion 520B of the detector shield 520 may reduce a gap between adjacent detector modules 200 in the detector array 300 to about 200 μm or less. The detector shield 520 may prevent electrical breakdown between adjacent detector modules 200 that may occur during controlled or uncontrolled power up or down sequences, if the high voltage supplied to the cathodes is powered in separate domains.

In various embodiments, the detector module 200 may also include an optional anti-scatter grid 530 disposed over the detector shield 520. The anti-scatter grid 530 may be in the form of a rectangular grid or parallel blades (e.g., wires) and may be electrically grounded. The anti-scatter layer 530 may comprise an electrically conductive material capable of withstanding a high voltage, such as tungsten or the like.

Figure 5C:
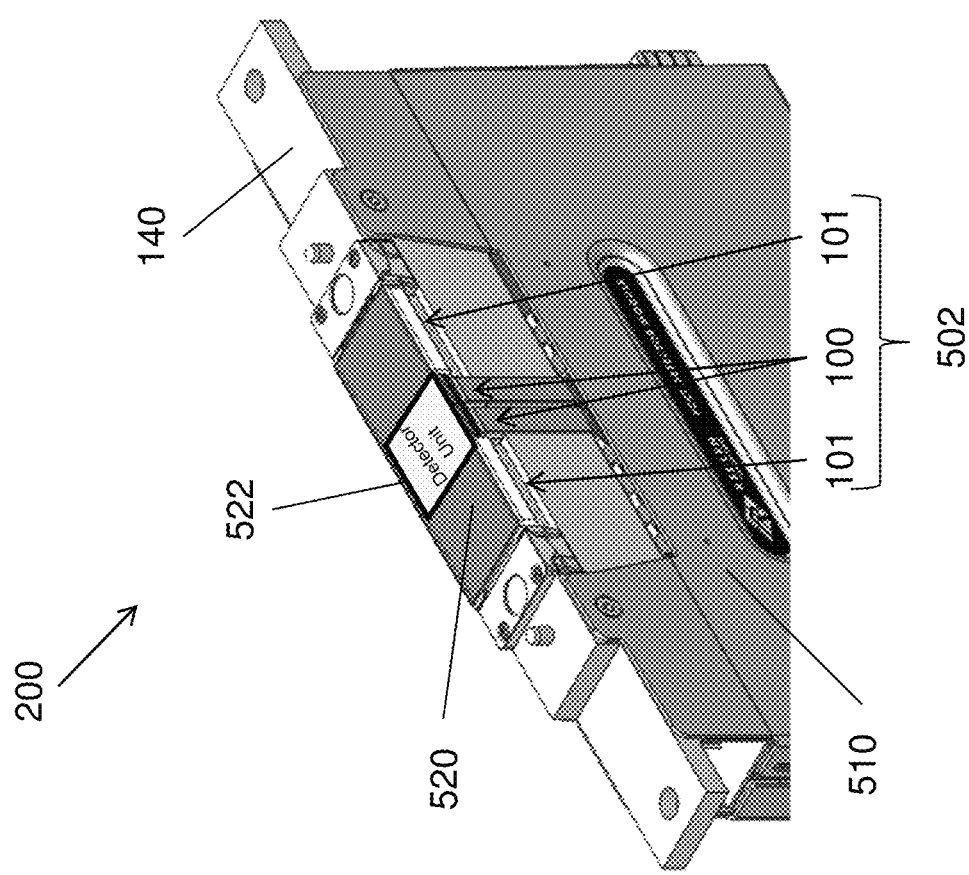
FIG. 5C is a perspective view of a detector module including a detector shield comprising alignment features, according to various embodiments of the present disclosure.

FIG. 5C is a perspective view of a detector module 200 including a detector shield 520 comprising one or more alignment features 522, according to various embodiments of the present disclosure. Referring to FIG. 5C, due to the optically opaque nature of the detector shield 520, it may be difficult to determine the location of the detector units 100. Therefore, it may be difficult to visually align the anti-scatter grid 530 shown in FIG. 5B with the detector units 100.

According to various embodiments of the present disclosure, the detector shield 520 may include one or more alignment features 522 that overlay the detector units 100. The alignment features 522 may allow for the location of the detector units 100 and or the dummy units 101 to be optically identified, such that the anti-scatter grid 530 may be properly aligned with the detector units 100. Further, the one or more alignment features 522 may allow for a visual determination as to whether the detector units 100 of adjacent modules 200 are arranged in a desired pixel pattern when assembled in a detector array, as shown in FIG. 6. The one or more alignment features 522 may comprise visible lines, shapes (e.g., rectangles) or other features printed in ink on the detector shield 520 or formed as grooves or protrusions in the detector shield 520.

Referring to FIG. 6, a detector array 300 can be formed by assembling multiple detector modules 200 on a detector array frame 310. The detector array frame 310 can be configured to provide attachment of a row of detector modules 200 such that the detection surfaces 504 of the radiation sensors 80 covered by the detector shield 520 collectively form a curved detection surface located within a cylindrical surface. Major surfaces of the module circuit boards 120 covered by the side shields 510 of adjacent detector modules 200 face each other in the detector array 300. The edges of the module circuit boards 120 containing the respective rows of radiation sensors 80 that face the detector array frame 310, such that the detection surfaces formed by the radiation sensors 80 are exposed through the frame 310. The detection surfaces 504 may be respectively covered by the first portions 520A of the detector shields 520.

The detector array 300 includes an assembly of multiple detector modules 200. The multiple detector modules 200 can be assembled such that rows of radiation sensors 80 attached to neighboring detector modules 200 abut each other, where the second portion 520B of the detector shield of one module 200 makes a direct surface contact with the exposed second side of the detector units 100 (e.g., of the radiation sensors 80 in the detector units 100). In particular, the second portions 520B of the detector shields 520 may physically separate and electrically isolate the radiation sensors 80 of adjacent detector modules 200.

The detector array 300 can be assembled by mounding the detector modules 200 to the frame 310. The detector array 300 can be repaired by removing a defective detector module 200 from the frame 310 without removing the functional detector modules 200 from the frame. The removed defective detector module 200 may be replaced with a functional detector module, or one or more defective radiation detector units 100 may be replaced in the defective detector module 200 as described above to repair the module 200 followed by replacing the repaired module 200 in the detector array 300.

Referring FIG. 6, the combination of the mounting frame 140 and the module circuit board 120 functions as a carrier unit for structurally holding the detector module 200 as a single structural component. If construction of an M×N array of radiation detector units 100 is desired, M detector modules 200 can be constructed such that a row of N radiation detector units 100 is attached to a module circuit board 120 with an accompanying mounting frame 140 within each detector module 200.

Generally, the radiation detector units 100 of the embodiments of the present disclosure can be constructed with a design that provides two-dimensional tiling with minimal gaps. The pixel pitch within each radiation detector units 100 can be maintained throughout the M×N array of radiation detector units 100 in the detector array 300 by minimizing gaps between neighboring pairs of radiation detector units 100 along the edge direction of the detector modules 200 and along directions perpendicular to the edge direction of the detector modules 200. Pixel pitch non-uniformity can be minimized across the entire M×N array of radiation detector units 100, and a substantially same pixel pitch can be provided across a large detection area. The methods of the present disclosure provide hierarchical construction of a large area detector array 300 from a plurality of radiation detector units 100. The number N of radiation detector units 100 that can be mounted on a detector module can be in a range from 2 to 32, such as from 4 to 16. The number M of detector modules 200 that can be mounted on a detector array frame 310 can be in a range from 2 to 64, such as from 4 to 32. In one embodiment, the radiation detector units 100 can be arranged in an orthogonal array (i.e., a rectangular array). However, other arrangements such as a hexagonal array or a similar two-dimensional pattern are also possible.

Figure 7:
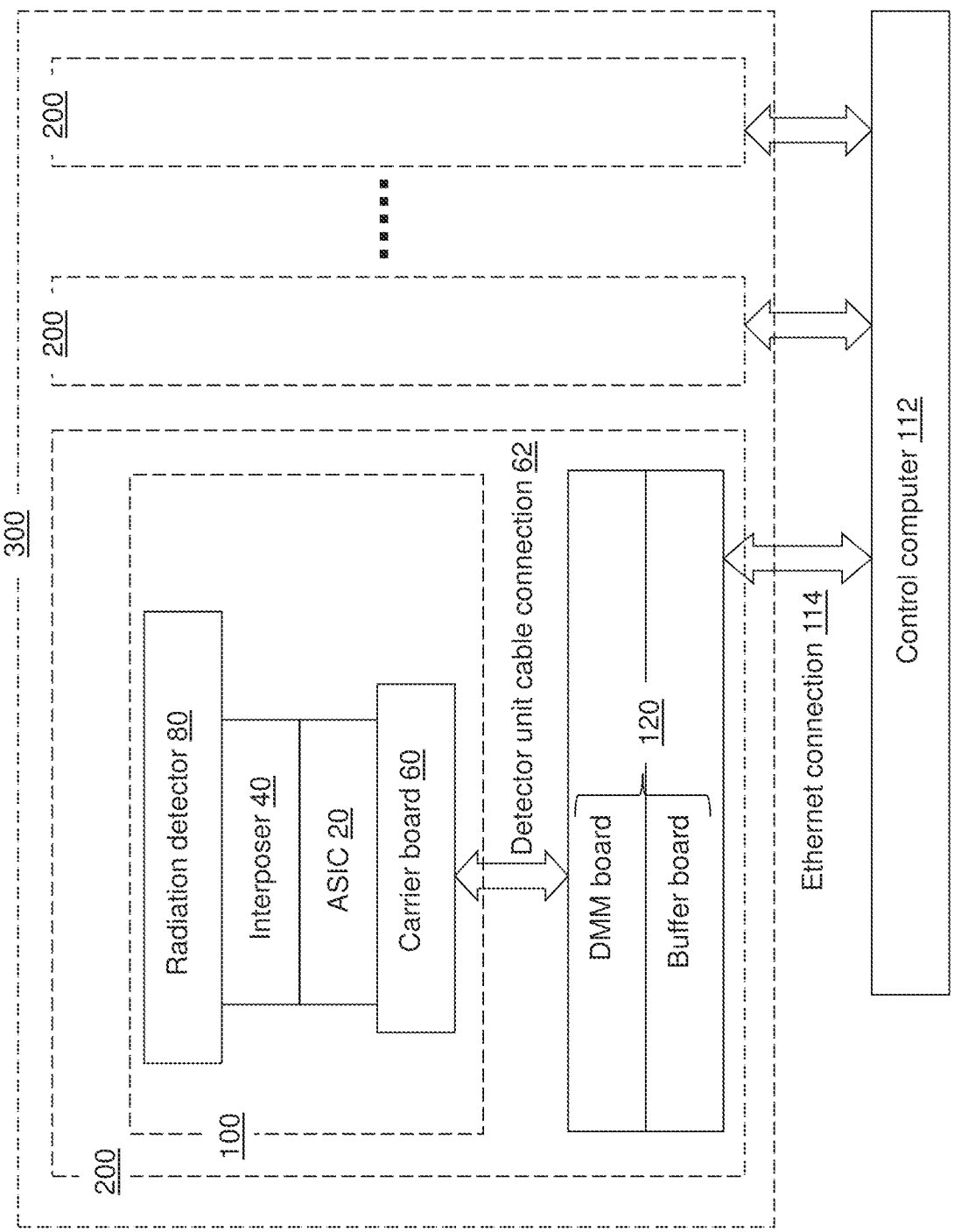
FIG. 7 is a schematic diagram illustrating the communication architecture of the detector array according to an embodiment of the present disclosure.

Referring to FIG. 7, a schematic diagram illustrating the communication architecture of the detector array 300 of the embodiments of the present disclosure is illustrated. A first level of electrical interconnection is provided within each radiation detector unit 100 between the sensing material pixels of the radiation sensors 80 and the electronic sense channels of the ASIC 20 via an interposer 40. A second level of electrical interconnection is provided between the radiation detector unit 100 and the module circuit board 120 of a detector module 200 by flexible cable assemblies 62. The module circuit board 120 can include a detector minimodule (DMM) board (which is also referred to as a detector unit interface board) that communicates with the radiation detector units 100 that are attached to the module circuit board 120, and a buffer board that interfaces with a control computer. The second level of electrical communication supports transmission of electrical power, control signals, and data signals between a module circuit board 120 and a set of radiation detector units 100.

A third level of electrical interconnection provides transmission of electrical power, control signals, and data signals between a module circuit board 120 and a control computer 112, and supports hierarchical integration of detector modules 200 into the detector array 300. The third level of electrical interconnections can be provided through rigid, multi-pin connectors directly mounted to a respective module circuit board 120, or through flex laminate cables terminated with a respective rigid multi-pin connector. The flex laminate cables can reduce the need for precision positioning of fixed connectors. Ethernet connection 114 may be employed to transmit control signals and data signals between the control computer 112 and the various module circuit boards 120.

Referring to all drawings of the present disclosure and according to an aspect of the present disclosure, a computed tomography system is provided. The computed tomography system comprises: a radiation source 104 configured to emit an X-ray; the detector array 300 configured to receive the X-ray from the radiation source 104 through an intervening space configured to contain an object 110 therein; and an image reconstruction system including a computer 112 configured to run an automated image reconstruction algorithm on detection signals generated from the detector array 300, which can be employed as the detector array 300 in the system of FIG. 1.

The devices of the embodiments of the present disclosure can be employed in various radiation detection systems including computed tomography (CT) imaging systems. Any direct conversion radiation sensors may be employed such as radiation sensors employing Si, Ge, GaAs, CdTe, CdZnTe, and/or other similar semiconductor materials. The radiation sensors 80 of the present disclosure are buttable on all four sides, and provides on-pitch radiation detection grid over a large detection area.

The radiation detectors of the present embodiments may used for medical imaging, such as in Low-Flux applications in Nuclear Medicine (NM), whether by Single Photon Emission Computed Tomography (SPECT) or by Positron Emission Tomography (PET), or as radiation detectors in High-Flux applications as in X-ray Computed Tomography (CT) for medical applications, and for non-medical imaging applications, such as in baggage security scanning and industrial inspection (e.g., non-destructive testing) applications.

While the disclosure has been described in terms of specific embodiments, it is evident in view of the foregoing description that numerous alternatives, modifications and variations will be apparent to those skilled in the art. Each of the embodiments described herein can be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

The invention claimed is:

1. A radiation detector module, comprising:
   a frame;
   a module circuit board connected to the frame;
   detector units that each comprise radiation sensors disposed above the frame and electrically connected to the module circuit board; and
   an optically and infrared radiation opaque, X-ray transparent, electrically insulating detector shield covering a top surface and at least one side surface of the radiation sensors.

2. The detector module of claim 1, wherein:
   the detector shield the detector shield is configured to block at least 99% of incident visible light and infrared radiation;
   is configured to transmit at least 99% of incident X-rays having an energy ranging from about 20 KeV to about 160 KeV; and
   has a dielectric strength of at least 2000 V/mil at a voltage of −1000V.

3. The detector module of claim 2, wherein the detector shield comprises tape or film formed of a polymeric material.

4. The detector module of claim 3, wherein the detector shield comprises a polyethylene terephthalate (PET) material or a polyimide material.

5. The detector module of claim 1, wherein:
   the top surfaces of the detector units form at least a part of the planar detection surface on top of the frame;
   a first portion of the detector shield covers a planar top surface of the detection surface; and
   a second portion of the detector shield extends and an angle from the first portion and covers a first side of the detector units.

6. The detector module of claim 5, wherein top surfaces of the radiation sensors form at least part of the detection surface.

7. The detector module of claim 5, wherein the second portion of the detector shield covers plural side surfaces of the radiation sensors.

8. The detector module of claim 5, further comprising dummy units located adjacent to the detector units and having top surfaces that form part of the detection surface, wherein:
   the dummy units are electrically inactive; and
   the first portion of the detector shield covers the top surfaces of the dummy units.

9. The detector module of claim 1, wherein the detector shield comprises an alignment feature configured to optically identify locations of the detector units.

10. The detector module of claim 1, wherein the detector shield is attached to the detector module by an adhesive, a friction fitting, or a clamp.

11. The detector module of claim 1, further comprising side shields disposed on the frame and configured to cover opposing sides of the module circuit board.

12. The detector module of claim 1, further comprising an electrically grounded, anti-scatter grid disposed over the detector shield.

13. The detector module of claim 12, wherein the anti-scatter layer comprises a metallic rectangular grid, blades, or wires.

14. The detector module of claim 1, wherein radiation sensors comprise a radiation-sensitive material selected from cadmium zinc telluride, cadmium telluride, gallium arsenide, silicon, and a scintillator material.

15. The detector module of claim 1, wherein:
   the module circuit board comprises a row of board-side connectors on each side of the circuit board; and
   each of the detector units further comprises an interposer, an application-specific integrated chip (ASIC), a carrier board, and a pair of flex cable assemblies electrically connected to one of the board-side connectors in each row.

16. The detector module of claim 1, wherein each detector module comprises at least two radiation sensors having a respective rectangular shape adjoined to each other with no gap or with a gap less than 3 mm.

17. A detector array, comprising:
   an array frame; and
   detector modules of claim 1 connected to the array frame, such that detection surfaces of the detector modules are exposed through the array frame.

18. The detector array of claim 16, wherein the detector shield prevents electrical contact and electrical breakdown between the radiation sensors of adjacent detector modules in the array frame.

19. The detector array of claim 16, wherein the array frame is curved, such that the detection surfaces of the detector modules collectively form a curved detection surface of the detection array.

20. An X-ray detection system, comprising:
   a radiation source configured to emit an X-ray;
   the detector array of claim 17, wherein the detector array is configured to receive the X-ray from the radiation source through an intervening space configured to contain an object therein; and
   an image reconstruction system including a computer configured to run an automated image reconstruction algorithm on detection signals generated from the detector array.

* * * * *